United States Patent [19]

Obiaya

[11] 4,141,955
[45] Feb. 27, 1979

[54] COMBUSTIBLE CONCENTRATION ANALYZER

[76] Inventor: Joseph O. Obiaya, 4773 Walford, #13, Warrensville Heights, Ohio 44128

[21] Appl. No.: 845,050

[22] Filed: Oct. 25, 1977

[51] Int. Cl.$^2$ ...................... G01N 27/16; H01L 27/16
[52] U.S. Cl. ..................................... 422/95; 136/224; 136/225
[58] Field of Search ............. 23/254 E, 232 E, 255 E; 136/224, 225, 226, 227

[56] References Cited

U.S. PATENT DOCUMENTS

| | | | |
|---|---|---|---|
| 1,321,063 | 11/1919 | Lamb et al. | 23/254 E X |
| 1,640,801 | 8/1927 | Petersen | 136/224 X |
| 2,073,249 | 3/1937 | Morgan et al. | 23/232 E |
| 2,234,128 | 3/1941 | Miller | 23/232 E |
| 2,531,592 | 11/1950 | Yant et al. | 23/232 E |
| 2,533,430 | 12/1950 | Chase | 23/255 E X |
| 3,138,436 | 6/1964 | Harmon | 23/254 E X |
| 3,960,500 | 6/1976 | Ross et al. | 23/255 E X |
| 4,029,472 | 6/1977 | Micheli et al. | 136/225 X |
| 4,063,898 | 12/1977 | Fisher | 23/255 E X |

Primary Examiner—Morris O. Wolk
Assistant Examiner—Arnold Turk
Attorney, Agent, or Firm—Watts, Hoffmann, Fisher & Heinke Co.

[57] ABSTRACT

Combustible element analyzer for determining the combustible element concentration of a sample gas. The sample is routed through an inlet conduit, mixed with a source of air, heated to an elevated temperature and analyzed by the combustible element analyzer. The analyzer includes a number of series connected thermocouples forming a thermopile. Exothermic reactions induced in the sample by catalyst elements create temperature variations along the thermopile. These variations cause a voltage difference along the thermopile whose value can be correlated to the combustible element concentration within the sample. Means are included for maintaining uniform sample flow past the analyzer and for maintaining analyzer calibration should the flow rate vary.

2 Claims, 7 Drawing Figures

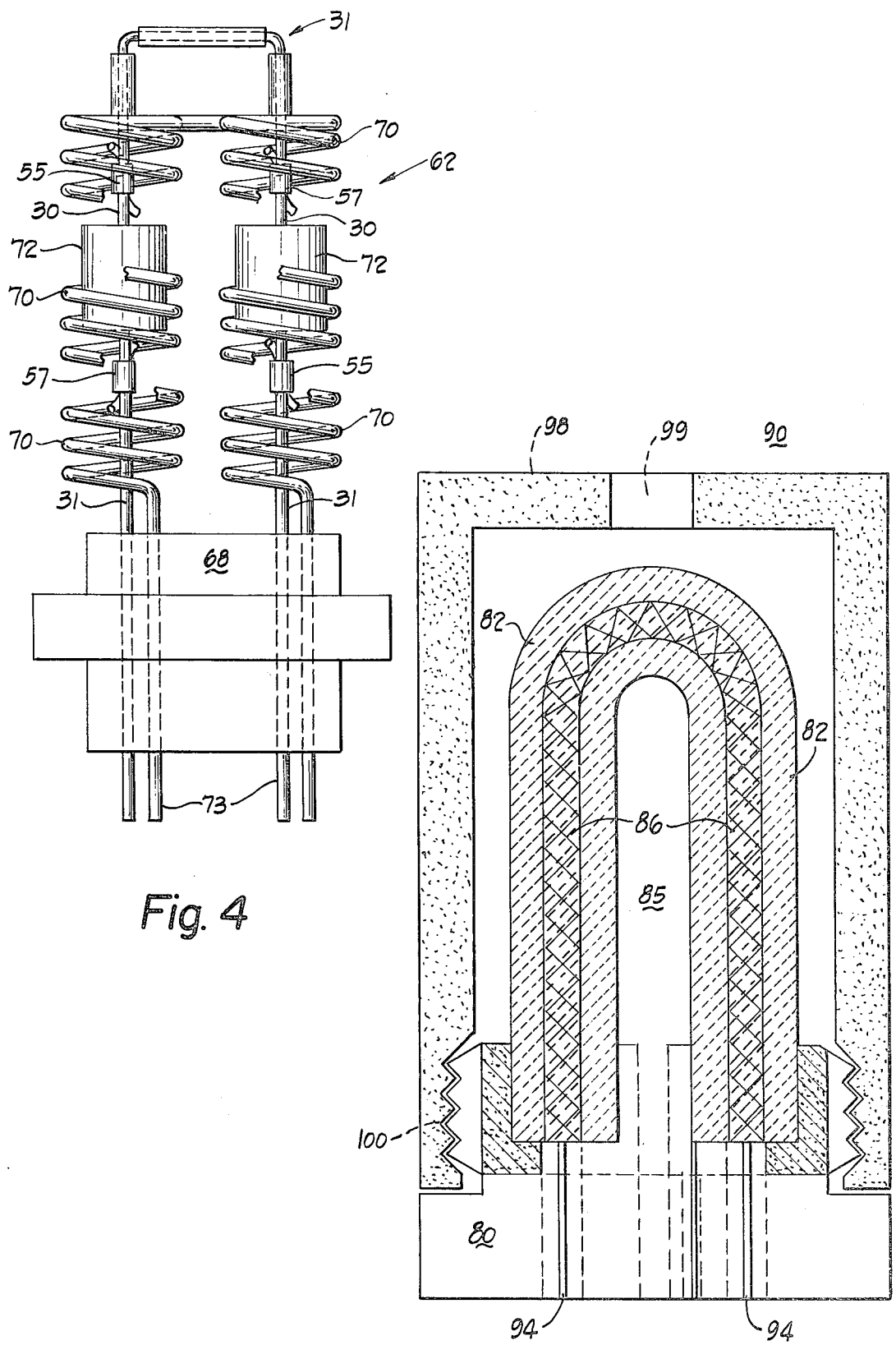

COMBUSTIBLE CONCENTRATION ANALYZER

BACKGROUND OF THE INVENTION

This invention relates to improved apparatus and techniques for monitoring the concentration of combustibles in a combustible fuel environment.

A combustible element analyzer monitors either the input or output from a combustion source and determines the percentage concentration of combustible elements in that sampling. To achieve this monitoring, a sample of the combustion process is obtained from a furnace or other source and forced past a combustion element analyzer, which forms the present invention.

Monitoring combustion element concentration provides information that aids in achieving combustion efficiency In the typical combustion process, an oxidation reaction occurs between oxygen ($O_2$) and an element or substance which readily combines with oxygen in an exothermic reaction. The end result, of course, is to obtain heat from this reaction and utilize that heat directly or transform it into other means of useful energy, and to measure the energy. The typical combustion reaction follows a well-defined stoichiometric relationship between the elements involved. If the concentration of the combustible element is higher that optimum level in the combustion chamber, the combustible element tends to retard the reaction. If the concentration of combustible element becomes too high, the oxidation may be extinguished. If, on the other hand, the combustible concentration is too low (that is, the oxygen is in too high a concentration) the combustion will go to completion but the energy given off in the form of heat tends to heat the excess air rather than be useful to the system. It has been found that by monitoring the reactions of the combustion process, it is possible to determine whether the combustion reaction is efficiently producing heat, or if steps need be taken to increase efficiency.

Another use for the combustible monitoring technique is to monitor pollutants. Since many pollutants are actually inefficiently burned combustibles, the combustible sensor can be utilized to determine whether changes need be made in an oxidation reaction process. The system therefore can be used to monitor automobile exhaust systems, industrial exhaust systems, and any other source of combustion products.

A presently available combustible sensor known as the Taguchi sensor or TGS, employs a solid-state device made of a sintered N-type metallic oxide produced from the iron, zinc and tin families. A heater coil is embedded in the oxide to bring the metallic oxide semiconductor device to operating temperature in the 150°–300° C. range. At this temperature, a functional relationship exists between the conductivity measured in the metallic heater coils and the combustible gas concentration in the sample. Utilization of this functional relationship allows determination of the combustible gas concentration.

The TGS sensor, however, involves serious shortcomings which the present invention adequately overcomes. The TGS apparatus is not intended for continuous accurate measurement of combustible gases, but rather it is utilized to trigger an alarm whenever a dangerous level of combustible gases exists. Since the heater coil is not only used to measure the combustible gas concentration but also is used to heat the element, signal drift becomes a major problem in the apparatus. The apparatus is further susceptible to interference from gases such as nitric oxide, sulphur dioxide, or water vapor, which can alter the results obtained.

SUMMARY OF THE INVENTION

The present invention provides a combustible element analyzer which through an electrochemical reaction determines the combustible gas concentration in a sample of gaseous fluid containing combustible elements. Any chemical reaction in which energy is released is called an exothermic reaction, as distinguished from an endothermic reaction in which energy is absorbed. One type of exothermic reaction is the combination of oxygen with another element to form a compound plus energy in the form of heat. Assuming an excess of oxygen available for the reaction, the relative concentration of combustibles in a gas sensor can be determined by reacting the sample with the oxygen and measuring the amount of heat given off in the reaction. As the combustible concentration increases, the heat given off will also increase.

The present invention uses a thermoelectric effect to measure the amount of heat released by the exothermic reaction. It is a well known principle that if two dissimilar metals are joined together and a heat difference applied at the junction of these metals, an electromotive force can be generated without a chemical reaction. If, for example, two dissimilar metal strips such as copper and iron, have their ends joined together and the temperatures at the two junctions of these metals are different, a current will develop in the circuit that the two strips form. The two metals joined in this fashion constitute a thermocouple.

The present invention comprises a number of thermocouples consisting of pairs of dissimilar metals joined in series within a combustible sensor analyzer to form a thermopile or sensing matrix. These pairs will be sensitive to temperature changes along the length of the matrix. If an exothermic reaction between a combustible and oxygen occurs at certain junction points along the length of sensing matrix of thermocouples, a voltage reading directly proportional to the element concentration will result.

As the combustible element sample from a furnace or other source passes over the series coupled thermocouples, no reaction occurs unless a catalyst is present to initiate it. To induce the exothermic reaction, a catalytic material is placed about certain junctions of the thermopiles in such a relationship as to create the exothermic reaction on these junctions which are called active junctions. To further induce the reaction, and eliminate $SO_2$ poisoning effects, heater elements are used to raise the ambient temperature surrounding those points. In the invention alternate thermocouple junctions are coated with a catalyst of platinum which is helpful in promoting the oxidation of a combustible to form a third element plus heat. The heat given off by the induced exothermic reaction will cause a rise in temperature at the selected junctions along the series connected thermocouples and thereby create a voltage in the matrix. The voltage difference produced along the length of the matrix is directly proportional to the heat given off in the catalytically induced exothermic reaction and by stoichiometric the stochiometric equation, it is possible to correlate the voltage produced to the combustible element concentration within the analyzer. Thus through proper calibration of an external electronic meter, it is possible to directly read the combustible's concentration within the sample source. By increasing the number of thermocouple junctions, it is possible to make the resulting analyzer more sensitive to smaller concentrations in gas content. If, for example, it is known that a low concentration of combustible is in the sample, a large number of thermocouple junctions will result in a substantial voltage flow even though the original concentration was small. With this knowledge a multirange sensing unit can be designed by means of the proper electrical interconnects to monitor gaseous content regardless of the range of concentration involved. The invention in this form allows the user to continuously monitor the combustible concentration and therefore overcomes the previously noted shortcoming of the TGS sensor, even when other background gases are present such as sulphur dioxide.

When the number of thermocouple junctions is small, it is probably more efficient to mechanically produce these junctions and mount them on an electrically insulating material. As the sensitivity requirements increase, it is more efficient to utilize a mass production-type arrangement for fabricating the device. To facilitate such production, a sputtering technique is useful whereby the various elements constituting the thermopile, the insulators, the heater elements, and the catalyst element are sprayed and/or sputter-etched upon a substrate in a fashion similar to integrated circuit fabrication. The fabrication process results in a number of advantageous improvements over the mechanical production technique: An increased number of junctions can be readily provided, resulting in greater system sensitivity to combustible element concentration; the noise levels in the system remain fixed and more junctions enhance the output signal to noise ratio of the system; less time is required for fabrication than in the mechanical technique; and it is easier in large scale production for the sputter technique to be used than the mechanical process. Thus it is seen that the new technique not only has numerous performance advantages over the prior art but also is susceptible to mass production techniques.

The combustible element analyzer of this invention has designed to operate in an industrial environment where many stray elements and dirt are in excess. In these circumstances the catalyst functions best at an elevated temperature in the range of 800° F. To achieve this elevated temperature, it is desirable to utilize heater elements in various places throughout the system. Once the sample of gas is obtained it is initially heated in a labyrinth contained in a manifold block whose temperature is kept constant at 400° F. To insure that the combustible elements are completely analyzed within the analysis chamber, a source of atmospheric air is also heated within the labyrinth to approximately 400° F. Near the combustible element analyzing matrix the sample gas is further increased in temperature to approximately 800° F. It has been determined that this temperature level causes the analyzer to function properly even though background gases such as sulphur dioxide, nitrogen oxide and water vapor are present within the system. This elevation in temperature thus has a two-fold affect, first, it raises the temperature of the exothermic reaction to a point at which the catalyst most efficiently causes the reaction to go to completion, and second, it causes the combustible element analyzer to operate more effectively in the industrial environment in which it served its greatest usefulness.

In a preferred configuration, the analyzer has an inlet port and an outlet port through which sample gases are caused to flow by a pressure drop within the system produced by any suitable means found appropriate for the system configuration. In an extremely dirty environment, it has been found expedient for a filter system to be inserted within the system to block dirt and other foreign elements from entering the combustible sensor apparatus. As the system operates, the filter element becomes clogged with dirt and a reduction in the pressure results. This reduction in pressure has adverse affects on a calibrated system due to decreased sample flow within the analyzer. It has been found, however, that it is possible to introduce a compensation device within the system to monitor changes in flow rate due to pressure changes within the system. As the flow rate within the system decreases, the combustible reaction decreases, thereby reducing the output from the combustible sensor. By inserting a compensation device within the system which produces an electrical voltage that increases in proportion to the reduced flow rate, this reduction in combustible sensor output can be compensated for. In actual operation a transducer sensitive to the pressure change (and thereby the flow rate) is inserted within the system. The transducer is arranged to provide an electrical output that increases as the pressure measure decreases. By adding this signal to the signal from the combustible element analyzer, it is possible to obtain a compensation system in which the final electrical output monitored accurately displays combustible concentration regardless of flow rate within the system. Through utilization of this technique, it is possible, therefore, to operate the system within an environment in which dirt and other foreign elements alter the flow rate.

The above and other features and advantages of the invention will become more apparent as the invention becomes better understood from the detailed description that follows, when considered in connection with the accompanying drawings.

BRIEF DESCRIPTION OF THE DRAWINGS

FIG. 4 depicts a functional combustible element analyzer formed by crimping together discreet thermocouple elements;

FIG. 5 is a sectional view of an improved oxygen concentration analyzer;

Detailed Description

Figure 1:
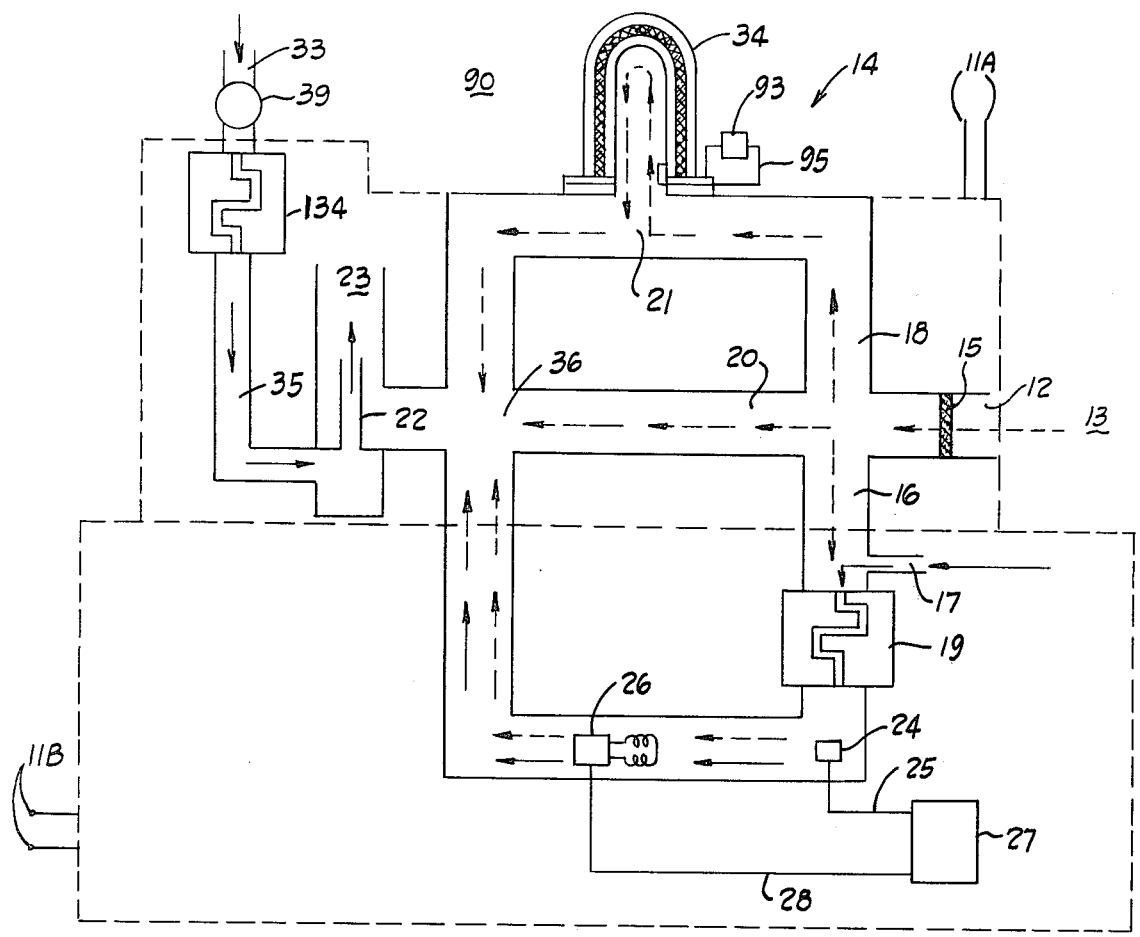
FIG. 1 is a schematic diagram of an oxygen concentration and combustible element concentration analyzing system embodying the present invention.

FIG. 1 presents a general schematic diagram of an oxygen concentration and combustible concentration analyzer comprising an inlet 12 for obtaining a sample of gas from a furnace or other sampling area 13, a conduit system 14 which divides into three portions 16, 18, and 20, and an outlet port 23 into which the three portions merge. Fluid flow within the conduit system 14 is maintained by means of an aspirator or eductor 22 located adjacent the outlet port. This configuration allows the gas to flow through the respective conduit portions, be analyzed by analyzers 26, 34 within the respective portions 16, 18, and be recombined and emitted from the outlet port 23.

The gaseous portion entering the conduit portion 16 will be tested for its combustible element content. It is combined with atmospheric air at an air inlet 17 in the conduit portion 16 and the combined flow then enters a heating labyrinth 19 which transfers ambient heat to the flow. After being heated in the labyrinth to a temperature of approximately 400° F., the gases comprising this portion of the sample are emitted from the heating labyrinth 19 and pass a pressure transmitter 24 which helps maintain proper calibration of the analyzer 26. After leaving the general area of the pressure sensor, the part of the sample passing through conduit portion 16 is tested by the combustible concentration analyzer 26 and is then recombined with the other portions of the gaseous sample.

A second portion of the gas sample to be analyzed by this system enters conduit portion 18 and travels along that conduit portion until it reaches an area 21 where the oxygen concentration analyzer 34 is located. A part of that sample gas enters the oxygen concentration analyzer 34 and travels along a generally U-shaped path until it again joins conduit portion 18. While within this confined area, a portion of oxygen within the gaseous sample interacts with the analyzer to produce an electrical output indicative of the oxygen concentration. The second sample portion then continues to travel along conduit portion 18 until it is reunited with the other gaseous elements.

The third conduit portion 20 serves to carry a third portion of the sample gas to the juncture 36 where the flows are recombined. This conduit facilitates gas flow and eliminates undesirable pressure variations within the system.

After reuniting at the juncture 36, the gases are swept from the system by the aspirator 22. Since the details of the aspirator are not part of this invention, it has been presented in the schematic form and may be one of a number of commercially available devices to produce the desired result. After analysis has been completed the sample is returned to the original source.

A final conduit 33 enters the system 14 to provide a source of compressed air to the aspirator 22. The compressed air passes through a pressure regulator 39 to maintain constant pressure in conduit 35 thereby insuring uniform aspirator operation. Uniform aspirator functioning results in uniform sample flow within the system 14, which is necessary for proper sensor calibration. The air is heated within a labyrinth heater 134 and passes through conduit 35 to the aspirator 22. If unheated compressed air is used in conduit 35 moisture condenses at the outlet port 23. Such condensation attracts dirt and dust particles which may clog the outlet port and interrupt sample flow through the system.

The entire conduit system 14 is heated to a temperature of 400° F. by block heater elements 11A and 11B. The precise mechanism for heating the system 14 to this level is not critical and can be accomplished in any commercially reasonable manner.

The labyrinth 19 of the combustible element analyzing portion of the system serves to transfer heat to the sample gas after it has been combined with a quantity of air at atmosphere pressure introduced through the inlet 17. In a preferred construction the labyrinth is either cast or machined to form an integral part of the combustible sample conduit path 16. The attainment of a 400° F. temperature of the gas is crucial in producing a catalytic reaction on the individual sensors of the combustibles analyzer, and since the sensor response is dependent upon the sample temperature, a reliable means of heating the sample fluid to a predetermined temperature within the system is a necessity. By including the labyrinth as a direct part of the combustible sample flow path, a reliable constant temperature of the sample can be assured by the ambient temperature of the labyrinth, which will facilitate calibrating the system. Passage of the sample through the labyrinth is an effective way to obtain final temperature of 400° F. After leaving the labyrinth 19 the sample passes the pressure sensor 24 and enters the region of the combustible concentration analyzer 26.

Figure 2:
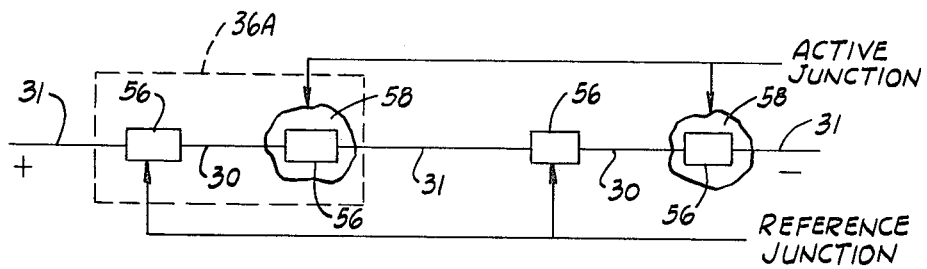
FIG. 2 is a schematic diagram of a number of series connected thermocouples for a combustible element analyzer.

As seen schematically in FIG. 2, the combustible concentration analyzer 26 comprises a number of series-connected thermo-couples 36A sensitive to temperature changes at their metallic junctions. This connection of thermo-couples forms a matrix arrangement (thermopile) whose shape can be varied. Each of the thermo-couples comprises a chromel element 30 and an alumel element 31 which are joined at junctions 56. While chromel and alumel have been chosen in the preferred embodiment of the invention other dissimilar metals can be chosen to form the thermo-couple. For example a segment of platinum could be joined to a segment of 90% platinum and 10% rhodium to produce the required effect. Also other percentages of the platinum-rhodium alloy could be chosen. At a chromel-alumel junction any temperature variation above the ambient temperature of the rest of the configuration will produce a current flow within the arrangement. To transform the chromel-alumel series connected thermo-couples into a combustible element analyzer, a platinum element 58 (see FIG. 2) which is a paste is coated upon alternate junctions. The platinum coated junction is referred to as an active or catalytic junction and the non-coated junction as a reference or non-catalytic junction.

The platinum element 58 induces an exothermic reaction within the combustible concentration analyzer. Platinum was chosen for two reasons; (a) the platinum will effectively catalyze a reaction between oxygen and a combustible element within the system when a high enough ambient temperature is maintained, and (b) the platinum catalyst element effectively withstands any degradation due to the presence of unwanted foreign elements which enter the system with the sample gas. For example, the platinum catalyst element is especially resistant to the poisonous effects of sulphur dioxide ($SO_2$) at elevated temperature above 800° F. With the platinum catalyst element in place the chromel-alumel pairs in combination with their crimping elements and the catalyst complete the construction of the matrix arrangement. While the platinum paste is preferred due to its operating characteristics in an environment with high sulfur dioxide concentrations, other substances such as a palladium paste can be used to catalyse the reaction.

Figure 3:
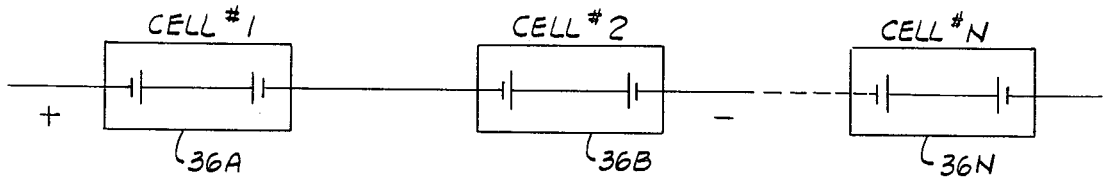
FIG. 3 is a diagram showing the functional equivalence between series connected thermocouples and series connected batteries.

As seen in FIG. 3, the combination of the series connected thermo-couples plus the catalytically induced exothermic reactions produces an effect similar to a series connection of batteries. Every active-reference junction pair can be thought of as an individual cell 36A, 36B and 36N which produces a voltage difference within the series connected system. With reference to FIGS. 2 and 3, the configuration of the chromel-alumel pairs depicted indicates a voltage increase from right to left. Each succeeding active-reference pair produces a voltage difference due to the exothermic reaction occuring at the active junction. The total system output from this configuration can be found by summing the individual voltage differences on the thermo-couple connections. As seen in FIG. 3 this would be equivalent to N times the voltage difference from one active-reference pair.

Reversing the order of the chromel 30 alumel 31 pairs in the sensor causes the electrical polarity of the system to reverse. If in FIG. 2 the chromel elements 30 were changed to alumel 31 and vice versa the voltage would increase from left to right. The sequence depicted in FIG. 3 is preferable, however, due to improved signal to noise ratio of that configuration.

One arrangement of the thermo-couple configured combustible analyzer is shown in FIG. 4. This analyzer comprises a base 68 and a series of connected thermo-couples 62 arranged in a U-shaped configuration. Mechanically, links of alumel and chromel are held together by a series of crimp materials 55 and 57 placed around the chromel-alumel elements to form a junction. In the present arrangement the crimp for a reference junction 55 is made of silver and the crimp for an active junction 57 made of platinum.

In the system shown in FIG. 4, a platinum catalyst material 58 (shown only in FIG. 2) is applied to alternate crimp junctions 57 within the system. In order to raise the ambient temperature of the thermo-couples to a range of approximately 800° F. (i.e. 400° F. higher than the sample entering the combustible sensor) a series of heating coils 70 are arranged coaxially with the thermo couple series connections. These heater coils are connected to a source of voltage and due to joule heating cause a rise in the ambient temperature surrounding the junctions. The 800° F. operating temperature is desirable primarily to eliminate $SO_2$ poisoning of the catalyst element 58. Since the heating elements are connected to a source of electrical energy, it is necessary that they be insulated electrically from the thermopile conduction matrix. For this reason a bead-like element 72 is imposed between the heater coils and the thermo-couple junctions. This element can be of any suitable material which will conduct heat while insulating the elements from electrical contact. In the preferred embodiment this bead insulation material is mullite and is bound to the heating coils 70 by a suitable contact cement.

The electrical leads to both the thermo-couple matrix and the heater coils 70 pass through the base 68 to a standard electrical pin connector 73 to achieve electrical insulation of the output signal of the combustion concentration analyzer from the heat coil.

Figure 6:
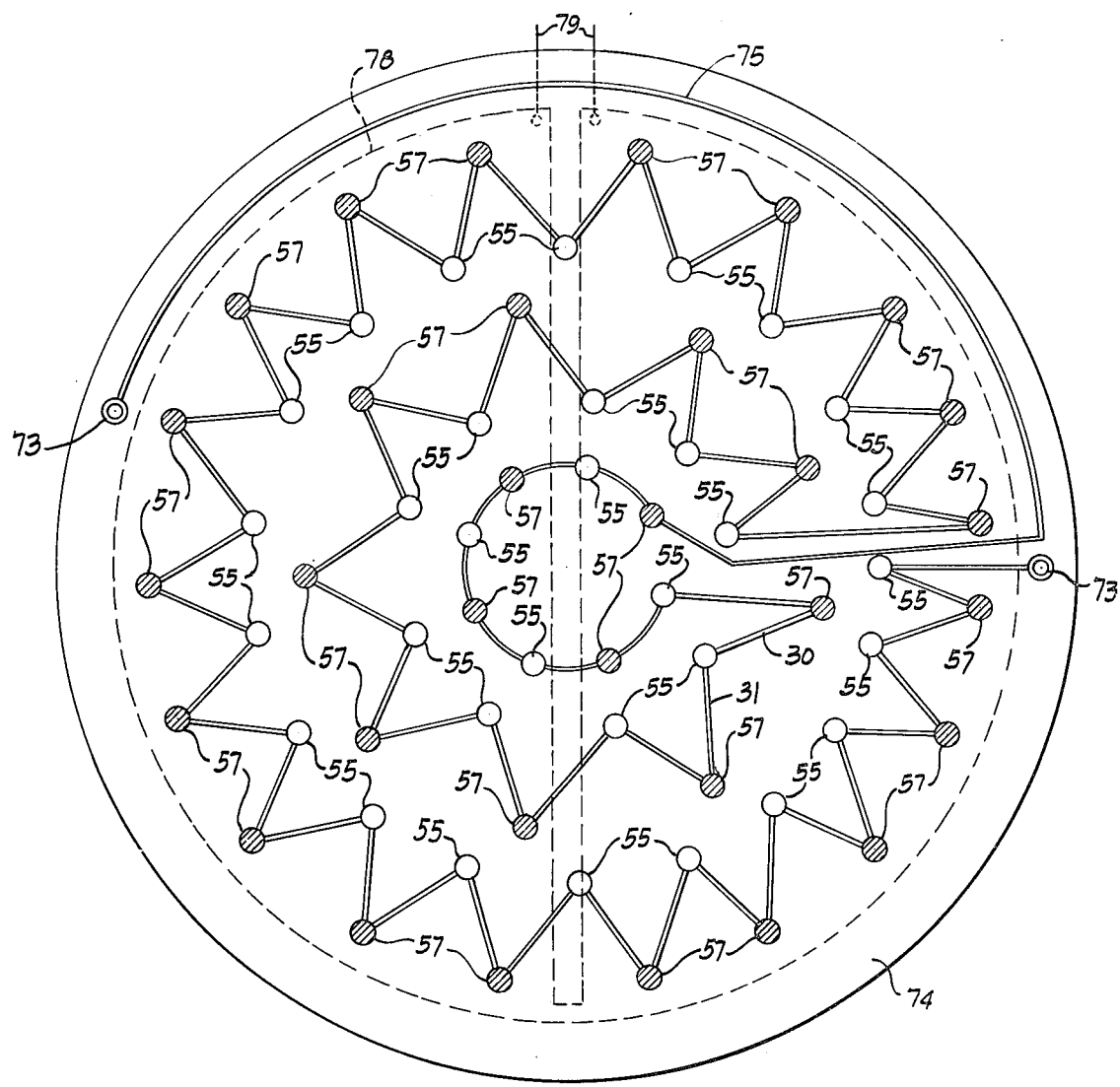
FIG. 6 is a plan view of a combustible element analyzer constructed using a masking technique which provides improved sensitivity readings.

A second version of the combustible element analyzer is shown in FIG. 6. This apparatus works on the same principal as that of FIG. 4 but posesses certain attributes which are superior. As seen in FIG. 6, a number of chromel 30 and alumel 31 pairs are sputter-etched in the form of a thermopile matrix. The alternating active junctions 57 of these pairs are coated with a catalyst material 58 which produces the exothermic reaction in a similar manner to the prior noted device. The difference between the two is the physical construction and fabrication technique involved. The analyzer of FIG. 6 is comprised of layers coated upon a substrate material 74. Through the use of a masking technique similar to those used in integrated circuit fabrication, the chromel-alumel and catalyst elements are successively sputter-etched onto the substrate material at desired locations to form an operating thermoplile matrix of thermo-couples. The precise order and configuration of the chromel-alumel and catalyst etching are not critical to system performance. The electrical interconnection circuit 75 is also sputtered onto the substrate material 74 in a pattern to connect the thermo-couple matrix to the connections 73. As in the arrangement of FIG. 4, it is necessary to again raise the temperature of the ambient conditions surrounding the chromel-alumel pairs to approximately 800° F. To attain this temperature, a resistance heating circuit 78 shown in phantom comprising a resistive element has been sputter-etched upon the substrate on the surface opposite to the combustible analysis matrix. In this way electrical insulation is readily obtained between the thermopile and contacts 70 to the heating circuit and as long as the substrate material is a good conductor of heat the ambient temperature surrounding the junctions 55 and 57 necessary for preventing $SO_2$ poisoning effect is achieved.

By using the masking fabrication process to produce the construction of FIG. 6, it is possible to achieve combustible concentration analyzer uniformity and increased production capabilities. It should also be noted that the increased number of alumel-chromel junctions increases the sensitivity to the point that even low levels of combustible concentration produce large enough signals for analysis.

The two combustible concentration analysis devices of FIGS. 4 and 6 produce a voltage at their pin connections 73 which is directly proportional to the concentration of the combustible in the sample gaseous fluid. This relationship follows from the functional correlation between heat given off and combustible concentration present at the active junctions. The voltage from the pin connections 73 of the matrix is then calibrated to yield the combustible element concentration. This calibration is done by utilizing a gas of known concentration to obtain reference readings upon a suitable volt meter 27. (see FIG. 1). These reference readings and the proportional relation between voltage and concentration allows interpolation to other concentration values. Since the particular reading device utilized is variable and not an element of the present invention, details of this calibration technique have been omitted.

As seen in FIG. 1, the design of the present system includes a filter or guard 15 which helps eliminate foreign elements such as dirt and unwanted particles which could adversely affect the operation of the total system. For industrial application where the gas carries particulate water or dirt, it has been found that the filter tends to clog with particles and a reduced flow rate within the conduit system 14 results due to reduced pressure differences along the system. If, for example, dirt and other elements within the sample environment cause the filter element to clog, the pressure variations from one portion of the conduit to the other vary to a lesser degree. This reduced pressure drop results in a reduced flow rate of the combustible sample past the combustible sample element analyzer 26 and adversely affects the system calibration. If, for example, the amount of combustibles passing by the analyzer 26 per unit time is reduced, fewer reactions can take place along the matrix thereby indicating a lower combustion concentration. This happens when, in fact, the combustible concentration has remained unchanged, and only the flow rate within the conduit 16 has been altered. To take into account the change in flow rate, a pressure sensor 24 has been introduced within the combustible analysis conduit 16.

The pressure transmitter 24 is one of a number of commercially available devices which sense changes in pressure. Attached to the pressure transmitter is an electrical interconnect 25 which transmits the output from the device 24 to the voltmeter 27. When the output from the pressure transmitter 24 is added to the combustible concentration analyzer output 28, a reading is produced that compensates for reduced flow rate due to the environment in which this system must operate. By way of example, if one uses a pressure transmitter which produces a voltage reading directly proportional to the pressure drop, one can add the output from this device interconnect 25 to the combustible concentration analyzer output interconnect 28 to produce a signal whose voltage is independent of flow rate within the conduit. Thus it is apparent that the system can be calibrated using one flow rate, but by utilization of a pressure sensor, will be accurate for all flow rates within the sensing capabilities of the combustion analyzer.

The upper conduit portion 18 in FIG. 1 provides a channel for the sample gas to be routed for oxygen concentration analysis. The sample gas flows through the upper conduit to the oxygen sensor 34. The oxygen sensor comprises a U-shaped or closed-end tubular member which forms a chamber 85 (see FIG. 5) within which the sample gas is allowed to flow. A base 80 serves as a support mount for an oxygen sensor heater element 86. Interwoven and layered upon opposite sides of the heater element 86 is a crystal-type structure of zirconium oxide 82.

Figure 7:
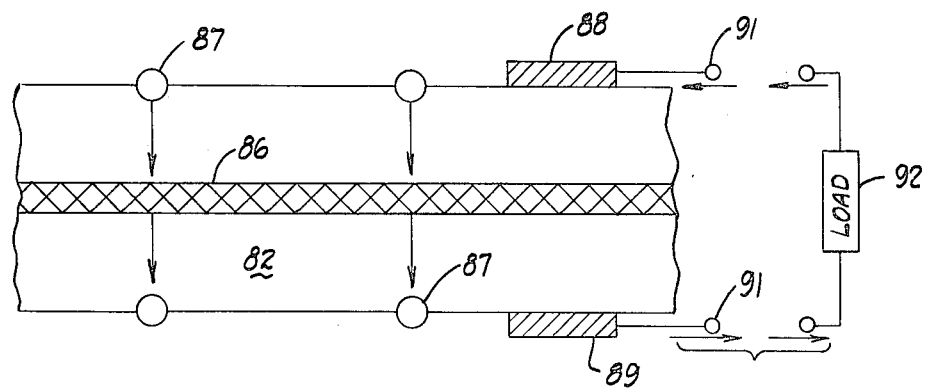
FIG. 7 is a schematic diagram showing oxygen ion migration within the oxygen concentration analyzer.

Functionally the oxygen concentration sensor operates using a voltaic reaction which involves the transfer of chemical energy into electrical energy. The zirconium oxide 82 is doped with a bivalent molecule such as magnezia, yttria, calcia to produce vacancies of minus 2 valence oxygen ions 87 (FIG. 7) within the crystal structure of the zirconium oxide.

By the use of platinum electrodes 88 and 89 (see FIG. 7) on opposite zirconium oxide surfaces one can induce a chemical reaction within the zirconium oxide (assuming proper ion concentration due to doping). The reaction at the cathode follows the relation:

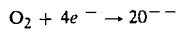

and at the anode:

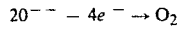

In the present invention the anode electrode 89 is in contact with the sample gas within the chamber 85 and the cathode electrode 88 is in contact with the surrounding atmosphere 90 which acts as a source of known oxygen concentration. If an external load circuit 92 is attached to the electrodes, the combination of the two half cell reactions at the cathode and anode cause oxygen ion migration and therefore a current to flow within the circuit.

The voltage created by this reaction is given by the Nernst equation:
$$E = RT/nF \ln(P_r/P_s)$$
where
- $R$ = Universal Gas Content
- $F$ = Faraday's Number
- $T$ = Absolute Temperature
- $P_r$ = Oxygen Partial Pressure of reference gas.
- $P_s$ = Oxygen Partial Pressure of sample gas.
- $n$ = number of electrons transferred in half cell equation.

Since the oxygen concentration of the surrounding atmosphere 90 is known, its partial pressure can be determined if atmospheric pressure is known. The voltage difference at a pair of electrode connections 91 can be measured by use of a suitable voltmeter 93 substituted in place of the load circuit 92. By combining this information with the other components of the Nernst equation, oxygen partial pressure in the sample can be calculated and through knowledge of the sample pressure the percent oxygen concentration calculated. Alternatively, knowledge that the voltage difference at the electrodes 88 and 89 is proportional to $\ln(1/P_s)$ enables the user to calibrate a suitable voltmeter by using a sample of known oxygen concentration.

The voltaic reaction occuring in the oxygen sensor is sensitive to temperature conditions. The most suitable lattice structure and ion concentration within the zirconium oxide occurs at approximately 1500° F. The present invention utilizes a heater element 86 directly embeded within the zirconium oxide 82. The heater element therefore gives structure to the zirconium oxide element without disrupting its well-defined crystal lattice structure. The element 86 is energized by power connections 94 and may be either A.C. or D.C. operated. Care must, of course, be taken to insure that the power connections 94 to the heater 86 are electrically insulated from the conductors 95 leading from the oxygen sensing electrodes 88 and 89 to the voltmeter 93. Surrounding the oxygen analyzer 34 is a insulation guard 98 as seen in FIG. 5. This guard screws onto the base 80 by means of a threaded coupling 100 and includes an opening 99 for receiving air from the surrounding atmosphere 90. The guard insures against excessive heat loss and therefore is made of appropriate heat insulating material.

After the oxygen concentration sample has been tested it returns to the oxygen conduit 18 and recombines with the samples from the other conduits 16 and 20 before being ejected out the outlet 23.

While the present invention has been described with particularity, it should be understood that various modifications and alterations may be made therein without departing from the spirit and scope of the invention set forth in the appended claims.

What is claimed is:

1. A combustible element analyzer comprising:
   (a) a substrate base formed from an electrically insulating material; said base including two configured opposite surfaces;
   (b) a plurality of series connected thermocouples attached to a first surface of said base, said thermocouples forming a thermopile matrix;
   (c) a plurality of catalyst material structures connected at spaced locations along said matrix to induce exothermic oxidation reactions at alternate junctions of said thermocouples among the components of a fluid sample thereby producing voltage differences along said matrix; said voltage differences adding in series to produce a total voltage signal larger than electrical noise within the thermopile, thereby enhancing the signal to noise ratio;

(d) means for electrically connecting the matrix to a monitor which will correlate matrix voltage to combustible gas concentration; and (e) a means for raising the ambient temperature of said matrix to a uniform value, said means attached to a second surface of said base material.

2. The combustible element analyzer of claim 1 wherein the catalyst element is platinum, and the matrix thermocouples are formed from chromel and alumel.

* * * * *